(12) United States Patent
Cahoon et al.

(10) Patent No.: US 6,864,403 B1
(45) Date of Patent: Mar. 8, 2005

(54) PLANT PROTEIN DISULFIDE ISOMERASES

(75) Inventors: Rebecca E. Cahoon, Wilmington, DE (US); Guo-Hua Miao, Hockessin, DE (US); Rafael Herrmann, Wilmington, DE (US); J. Antoni Rafalski, Wilmington, DE (US); Billy F. McCutchen, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/417,251

(22) Filed: Oct. 13, 1999

Related U.S. Application Data

(60) Provisional application No. 60/104,426, filed on Oct. 15, 1998.

(51) Int. Cl.[7] ............................. A01H 1/00; C12Q 1/68; G01N 33/573; C12N 15/82; C07H 21/04
(52) U.S. Cl. ............................ 800/278; 435/6; 435/7.4; 435/91.1; 435/468; 536/23.1; 536/23.6
(58) Field of Search ............................. 435/6, 7.4, 69.1, 435/70.1, 91.1, 468; 536/23.1, 24.3, 23.6; 800/278

(56) References Cited

PUBLICATIONS

David Gerhold et al., It's the genes! EST access to human genome content, BIOESSAYS, vol. 18, No. 12, pp. 973–981.*
Timothy N. C. Wells et al., The chemokine information source: identification and characterization of novel chemokines using the WorldWideWeb and Expressed Sequence Tag Databases, Journal of Leukocyte Biology, vol. 61, May 1997, pp. 545–550.*
Robert B. Russell et al., Structural Features can be Unconserved in Proteins with Similar Folds, J. Mol. Biol. (1994), 244, pp. 332–350.*
Tetsuya Ookura et al., Biochemical and Biophysical Research Communications, vol. 213:746–751, 1995, Active Site Peptides with CXXC MOTIF on Map–Resin can Mimic Protein Disulfide Isomerase Activity.
McKay et al. (1995) Insect Biochem. Mol. Biol. 25:647–654.
Koivunen et al. (1996) Biochem. J. 316:599–605.
Koivunen et al. (1997) Genomics 42:397–404.
Mazzarella et al. (1990) J. Biol. Chem. 265:1094–1101.
Shorrosh and Dixon (1992) Plant J. 2:51–58.
Chaudhuri et al. (1992) Biochem. J. 281:645–650.
Wong and Bateman (1994) Gene 150:175–179.
Kim and Mayfield (1997) Science 278:1954–1957.
NCBI General Identifier No. 4289796.
NCBI General Identifier No. 4827500.
NCBI General Identifier No. 5124153.
NCBI General Identifier No. 5325044.
NCBI General Identifier No. 5361231.
NCBI General Identifier No. 5525515.
NCBI General Identifier No. 5597319.
NCBI General Identifier No. 5650368.
NCBI General Identifier No. 5688597.
NCBI General Identifier No. 5714111.
NCBI General Identifier No. 5770161.
NCBI General Identifier No. 5804735.
NCBI General Identifier No. 1709618.
Biosci. Biotechnol. Biochem. No. 58(8), pp. 1424–1429 (1994).
NCBI General Identifier No. 129726.
Biochem. Biophys. Res. Commun. 146(3), pp. 1485–1492 (1987).
NCBI General Identifier No. 2708314.
NCBI General Identifier No. 4678297.

* cited by examiner

Primary Examiner—Sean McGarry
Assistant Examiner—Jane Zara

(57) ABSTRACT

This invention relates to an isolated nucleic acid fragment encoding a protein disulfide isomerase. The invention also relates to the construction of a chimeric gene encoding all or a portion of the protein disulfide isomerase, in sense or antisense orientation, wherein expression of the chimeric gene results in production of altered levels of the protein disulfide isomerase in a transformed host cell.

14 Claims, No Drawings

SEQUENCE LISTING

<160> NUMBER OF SEQ ID NOS: 20

<210> SEQ ID NO 1
<211> LENGTH: 504
<212> TYPE: DNA
<213> ORGANISM: Zea mays
<220> FEATURE:
<221> NAME/KEY: unsure
<222> LOCATION: (463)
<223> OTHER INFORMATION: n is a, c, g or t
<220> FEATURE:
<221> NAME/KEY: unsure
<222> LOCATION: (469)
<223> OTHER INFORMATION: n is a, c, g or t
<220> FEATURE:
<221> NAME/KEY: unsure
<222> LOCATION: (471)
<223> OTHER INFORMATION: n is a, c, g or t
<220> FEATURE:
<221> NAME/KEY: unsure
<222> LOCATION: (496)
<223> OTHER INFORMATION: n is a, c, g or t

<400> SEQUENCE: 1

```
tgcctgccct gtcctgtcct gttcagcgga accttctctt tgtgttttat aggttacccc      60
gtcaaaaaga cagcccatca tgcaccacaa gaagatcgcc tgcagcttca tggctgctct     120
ggctgcctat gcctctgctg ccgactcaga tgttcatcag ctaaccaagg acaccttcga     180
ggagtttgtc aagtccaaca atctcgtcct cgctgagttc tttgctccct ggtgcggtca     240
ctgcaaggcc ctcgccccg agtacgagga ggccgccaca actctcaagg agaagaacat      300
caagcttgcc aagattgact gcactgagga gtccgacctc tgcaaagacc agggcgtcga     360
gggttacccc accctcaagg tcttccgtgg tcttgacaat gtcactccct actctggcca     420
gcgtaaggcc gctggtatca ttctacatga ttaagagttc ctncccggng nttcatttta     480
caaagggaac cctcgngggt ttaa                                             504
```

<210> SEQ ID NO 2
<211> LENGTH: 110
<212> TYPE: PRT
<213> ORGANISM: Zea mays

<400> SEQUENCE: 2

```
Met Ala Ala Leu Ala Ala Tyr Ala Ser Ala Ala Asp Ser Asp Val His
  1               5                  10                  15
Gln Leu Thr Lys Asp Thr Phe Glu Glu Phe Val Lys Ser Asn Asn Leu
             20                  25                  30
Val Leu Ala Glu Phe Phe Ala Pro Trp Cys Gly His Cys Lys Ala Leu
         35                  40                  45
Ala Pro Glu Tyr Glu Glu Ala Ala Thr Thr Leu Lys Glu Lys Asn Ile
     50                  55                  60
Lys Leu Ala Lys Ile Asp Cys Thr Glu Glu Ser Asp Leu Cys Lys Asp
 65                  70                  75                  80
Gln Gly Val Glu Gly Tyr Pro Thr Leu Lys Val Phe Arg Gly Leu Asp
                 85                  90                  95
Asn Val Thr Pro Tyr Ser Gly Gln Arg Lys Ala Ala Gly Ile
                100                 105                 110
```

<210> SEQ ID NO 3
<211> LENGTH: 505
<212> TYPE: DNA

<213> ORGANISM: Glycine max
<220> FEATURE:
<221> NAME/KEY: unsure
<222> LOCATION: (503)
<223> OTHER INFORMATION: n is a, c, g or t

<400> SEQUENCE: 3

```
tctttctggt actccacctg gtattgttgt tgaagatcgt aataccaata aaaattatgt      60
ttatccacaa gctaatgaaa ttactgaaga tgcattacgt gcacatttac aaggttatgt    120
tgatggtaca cttcaaccca ctgtcaaatc tgaagaaatc ccagaaaaac aagatggtcc    180
agtttatgta ctcgtgggta aaatttttga atccattgtt atggatgaaa ctaaagatgt    240
attagttgaa ttttatgcac catggtgtgg acattgtaaa acattagctc ccaaatacga    300
tgcattaggt gaatcattca gtcaaaccc caatgtcatt attgccaaga ttgatgccac    360
tgcaaatgat accctgttg atattcaagg tttccccact attatctatt ggccagctaa    420
taataagaaa aatccaatta catatgaagg tgaacgtact gaatcagcac ttgctgcatt    480
tgtacgtgaa aaatggtcaa cantt                                          505
```

<210> SEQ ID NO 4
<211> LENGTH: 158
<212> TYPE: PRT
<213> ORGANISM: Glycine max

<400> SEQUENCE: 4

```
Pro Gly Ile Val Val Glu Asp Arg Asn Thr Asn Lys Asn Tyr Val Tyr
 1               5                  10                  15

Pro Gln Ala Asn Glu Ile Thr Glu Asp Ala Leu Arg Ala His Leu Gln
             20                  25                  30

Gly Tyr Val Asp Gly Thr Leu Gln Pro Thr Val Lys Ser Glu Glu Ile
         35                  40                  45

Pro Glu Lys Gln Asp Gly Pro Val Tyr Val Leu Val Gly Lys Asn Phe
     50                  55                  60

Glu Ser Ile Val Met Asp Glu Thr Lys Asp Val Leu Val Glu Phe Tyr
 65                  70                  75                  80

Ala Pro Trp Cys Gly His Cys Lys Thr Leu Ala Pro Lys Tyr Asp Ala
                 85                  90                  95

Leu Gly Glu Ser Phe Lys Ser Asn Pro Asn Val Ile Ile Ala Lys Ile
            100                 105                 110

Asp Ala Thr Ala Asn Asp Thr Pro Val Asp Ile Gln Gly Phe Pro Thr
        115                 120                 125

Ile Ile Tyr Trp Pro Ala Asn Asn Lys Lys Asn Pro Ile Thr Tyr Glu
    130                 135                 140

Gly Glu Arg Thr Glu Ser Ala Leu Ala Ala Phe Val Arg Glu
145                 150                 155
```

<210> SEQ ID NO 5
<211> LENGTH: 1692
<212> TYPE: DNA
<213> ORGANISM: Zea mays

<400> SEQUENCE: 5

```
gcacgaggcg cggcggagat cgaatcgagc gcccgccacg gcgatggcga ctagagtcct      60
gccgccggct ctgctctctt tcatactcct cctgctgctc tcgctctcag cccgcgacac    120
cgtcgccgcg ggcgaggatt tcccacgcga cgggcgggtg atcgacctcg acgacagcaa    180
tttcgaggcg gcgctgggcg ccatcgactt tctcttcgtc gacttctacg ccccttggtg    240
```

```
cggccactgc aagagacttg cgcccgagtt agatgaagct gcaccggtgt tgtcagggtt      300
gagtgagcct attgttgttg ccaaagtcaa cgctgataaa tacagaaaac tcggatcaaa      360
atatggagtg gatgggttcc ctaccctcat gctctttatc catggtgttc caattgaata      420
cactggttcg aggaaagctg accagcttgt ccgcaatctg aagaagttcg tttcgccaga      480
tgtttctatc cttgagtcag attctgcgat aaagaacttt gttgagaatg ctgggataag      540
ctttccgata ttccttggtt ttgggggtgaa tgactcattg attgctgagt atggaaggaa      600
atacaagaaa agagcctggt tgctgttgc taaagatttc tctgaggaca tcatggtagc       660
ctatgaattt gataaggttc cagcactagt tgctatccat ccaaagtata aggaacagag      720
tttgttctat ggcccatttg aagaaaattt cttagaagat tttgtacggc aatcccttct      780 cccctttggtt gtcccaatca atacagagac actaaaaatg ctgaatgatg atcagaggaa      840
agttgttctc acaatttttgg aggatgattc agatgaaaac tctacgcaac tggtaaagat      900
tttgcgatct gctgctaatg caaaccgtga tttggtgttt ggatatgttg gaatcaagca      960
atgggatggg tttgtggaga cttttgatgt ttccaagagc tcacagctgc caaagctact     1020
tgtgtgggat agagatgagg agtatgagct agtggatggt tcagagagat tagaagaagg     1080
tgaccaagca tctcaaataa gccaattcct tgagggatac agagcaggaa gaacaacaaa     1140
gaagaaaatc accggcccctt ctttcatggg tttcctgaac tctctggtca gcctgaactc     1200
gctgtacatc cttatatttg tcatcgcccct tctgtttgtc atggtgtact ttgctgggca     1260
agatgatact cctcagccaa gacgaattca cgaagagtga tgaaagcttg ttgggcttct     1320
tgcacctaaa gatggctaat ctaccgggag attagctttt gtattaattg tacaaaagct     1380
tcaactgacg caagtcgtga agagtggttt tggcaatttg gccattcatg ctgagtttct     1440
tcaatctcta ttggcgacat caatttctgc atcctgccta tttgtgtttc tgctttgtgc     1500
ccttcaattt gttctttaat ttagagctta gaaattagcc tctgcctgtg tattctggaa     1560
cctgccattc cagagtccat ttctgtgaaa atatatttat tattatcata ctctgctacc     1620
gagcttttgt acaattaata caggatatat agactgttct ggtgcacaaa aaaaaaaaga     1680
aaaaaaaaaa aa                                                         1692
```

<210> SEQ ID NO 6
<211> LENGTH: 418
<212> TYPE: PRT
<213> ORGANISM: Zea mays

<400> SEQUENCE: 6

```
Met Ala Thr Arg Val Leu Pro Pro Ala Leu Leu Ser Phe Ile Leu Leu
  1               5                  10                  15

Leu Leu Leu Ser Leu Ser Ala Arg Asp Thr Val Ala Ala Gly Glu Asp
             20                  25                  30

Phe Pro Arg Asp Gly Arg Val Ile Asp Leu Asp Asp Ser Asn Phe Glu
         35                  40                  45

Ala Ala Leu Gly Ala Ile Asp Phe Leu Phe Val Asp Phe Tyr Ala Pro
     50                  55                  60

Trp Cys Gly His Cys Lys Arg Leu Ala Pro Glu Leu Asp Glu Ala Ala
 65                  70                  75                  80

Pro Val Leu Ser Gly Leu Ser Glu Pro Ile Val Val Ala Lys Val Asn
                 85                  90                  95

Ala Asp Lys Tyr Arg Lys Leu Gly Ser Lys Tyr Gly Val Asp Gly Phe
            100                 105                 110
```

-continued

```
Pro Thr Leu Met Leu Phe Ile His Gly Val Pro Ile Glu Tyr Thr Gly
        115                 120                 125
Ser Arg Lys Ala Asp Gln Leu Val Arg Asn Leu Lys Lys Phe Val Ser
        130                 135                 140
Pro Asp Val Ser Ile Leu Glu Ser Asp Ser Ala Ile Lys Asn Phe Val
145                 150                 155                 160
Glu Asn Ala Gly Ile Ser Phe Pro Ile Phe Leu Gly Phe Gly Val Asn
                165                 170                 175
Asp Ser Leu Ile Ala Glu Tyr Gly Arg Lys Tyr Lys Lys Arg Ala Trp
                180                 185                 190
Phe Ala Val Ala Lys Asp Phe Ser Glu Asp Ile Met Val Ala Tyr Glu
        195                 200                 205
Phe Asp Lys Val Pro Ala Leu Val Ala Ile His Pro Lys Tyr Lys Glu
        210                 215                 220
Gln Ser Leu Phe Tyr Gly Pro Phe Glu Glu Asn Phe Leu Glu Asp Phe
225                 230                 235                 240
Val Arg Gln Ser Leu Leu Pro Leu Val Val Pro Ile Asn Thr Glu Thr
                245                 250                 255
Leu Lys Met Leu Asn Asp Asp Gln Arg Lys Val Val Leu Thr Ile Leu
                260                 265                 270
Glu Asp Asp Ser Asp Glu Asn Ser Thr Gln Leu Val Lys Ile Leu Arg
        275                 280                 285
Ser Ala Ala Asn Ala Asn Arg Asp Leu Val Phe Gly Tyr Val Gly Ile
        290                 295                 300
Lys Gln Trp Asp Gly Phe Val Glu Thr Phe Asp Val Ser Lys Ser Ser
305                 310                 315                 320
Gln Leu Pro Lys Leu Leu Val Trp Asp Arg Asp Glu Glu Tyr Glu Leu
                325                 330                 335
Val Asp Gly Ser Glu Arg Leu Glu Glu Gly Asp Gln Ala Ser Gln Ile
                340                 345                 350
Ser Gln Phe Leu Glu Gly Tyr Arg Ala Gly Arg Thr Thr Lys Lys Lys
        355                 360                 365
Ile Thr Gly Pro Ser Phe Met Gly Phe Leu Asn Ser Leu Val Ser Leu
        370                 375                 380
Asn Ser Leu Tyr Ile Leu Ile Phe Val Ile Ala Leu Leu Phe Val Met
385                 390                 395                 400
Val Tyr Phe Ala Gly Gln Asp Asp Thr Pro Gln Pro Arg Arg Ile His
                405                 410                 415
Glu Glu
```

<210> SEQ ID NO 7
<211> LENGTH: 1774
<212> TYPE: DNA
<213> ORGANISM: Momordica charantia

<400> SEQUENCE: 7

| | |
|---|---|
| gcacgaggag ccggatgcgg cggccggtgc ttccgctcat cgtcacctcc ccgactttga | 60 |
| tggttttgag ggaggtgccg aggacgagga ttttggggac ttctccgatt ttgaggactc | 120 |
| ggatgctgat cgggatgagt acaaggcgcc ggaggtggac gagaaggatg tcgtcgtgtt | 180 |
| gaaggagggt aacttcagcg atttcgtgga agaaccggg tttgttatgg tggagttta | 240 |
| cgctccctgg tgtggtcact gccaggcgct ggcgccggag tatgctgctg ccgccactga | 300 |
| attgaaaggc gagaacgtgg ttttggcgaa ggttgatgcg acggaggaga atgaattgtc | 360 |

```
gcagaagtac gacgttcaag gatttccgac tgtttatttc tttgccgatg gagtccacaa    420
gtcttaccct ggacagcgga ccaaggatgc tatagtaacc tggatcaaga agaagatcgg    480
acctggtatt tacaacataa cttcggtgga agatgctgaa cgcatactga cttctgagac    540
taaagttgtt cttggttacc tgaactcctt ggtgggccct gagagcaatg agcttgctgc    600
tgcttcaaga ctggaagatg atgtcaactt ttaccaaacg gtggatcctg aagtggccaa    660
gcttttccac attgaagctt cagcaaaacg ccctgccttg gtattgctta agaaggaggc    720
tgaaaaactg aaccgctttg atggcgagtt ttctaagtct gcaattgctg aatttgtgtt    780
tgccaataag cttccattag ttacaaagtt tacgagagaa agcgcaccat tgattttcga    840
aagttcaatt aagaaacagt tgattctatt tgcgatttca atgattcag agaaactaat    900
ccccatattt gaagagtcgt cgaagtcttt taaaggaaag cttattttcg tttatgtgga    960
aattgacaat gaagatgttg gaaagccggt atcagaatac tttggcatta gtggcaatgg   1020
tccagaggtt cttggataca ctggaaatga ggacagcaag aaatttgtgc ttgctaagga   1080
agttactttg gataatatta aggctttcgg agaaaatttc ttggaagaca gttaaaaacc   1140
cttttataag tcagatccca ttcctgagac taatgatggt gacgtgaaag tagtggttgg   1200
agacaacttc gacaatattg ttttagatga atcgaaggat gttctcctcg agatctatgc   1260
tccttggtgt gggcattgcc aagcactgga accaacttat aacaagcttg ccaaacattt   1320
acgtggcatc gattcacttg tcattgctaa gatggatggc acaacaaatg aacatccccg   1380
ggcgaagtcc gatggattcc caacaattct gttttttccca gctggaaaca agagctttga   1440
ccctatcact gtcgataccg atcgtaccgt tgtggcactg tacaaattca tcaagaaaaa   1500
tgcatccatc cctttcaagc tacagaagcc agtttcgagt ccgaaagccg taagttctga   1560
agccaaatct ggtgatgcca agagagccc aaagagcagc accactgacg taaggatga   1620
attgtgaaga cttcttaaat agttttgtaa gttattatcc catctttat gcactttttg   1680
cagctgccag attttagac catatggaga gactagaaat taaaagaaaa tgttttttc   1740
cctttctct tagaaaaaa aaaaaaaaa aaaa                                  1774

<210> SEQ ID NO 8
<211> LENGTH: 541
<212> TYPE: PRT
<213> ORGANISM: Momordica charantia

<400> SEQUENCE: 8

His Glu Glu Pro Asp Ala Ala Gly Ala Ser Ala His Arg His Leu
  1               5                  10                  15

Pro Asp Phe Asp Gly Phe Glu Gly Gly Ala Glu Asp Glu Asp Phe Gly
                 20                  25                  30

Asp Phe Ser Asp Phe Glu Asp Ser Asp Ala Asp Arg Asp Glu Tyr Lys
             35                  40                  45

Ala Pro Glu Val Asp Glu Lys Asp Val Val Leu Lys Glu Gly Asn
         50                  55                  60

Phe Ser Asp Phe Val Glu Lys Asn Arg Phe Val Met Val Glu Phe Tyr
 65                  70                  75                  80

Ala Pro Trp Cys Gly His Cys Gln Ala Leu Ala Pro Glu Tyr Ala Ala
                 85                  90                  95

Ala Ala Thr Glu Leu Lys Gly Glu Asn Val Val Leu Ala Lys Val Asp
            100                 105                 110

Ala Thr Glu Glu Asn Glu Leu Ser Gln Lys Tyr Asp Val Gln Gly Phe
```

-continued

```
            115                 120                 125
Pro Thr Val Tyr Phe Phe Ala Asp Gly Val His Lys Ser Tyr Pro Gly
130                 135                 140
Gln Arg Thr Lys Asp Ala Ile Val Thr Trp Ile Lys Lys Ile Gly
145                 150                 155                 160
Pro Gly Ile Tyr Asn Ile Thr Ser Val Glu Asp Ala Glu Arg Ile Leu
                165                 170                 175
Thr Ser Glu Thr Lys Val Val Leu Gly Tyr Leu Asn Ser Leu Val Gly
            180                 185                 190
Pro Glu Ser Asn Glu Leu Ala Ala Ala Ser Arg Leu Glu Asp Asp Val
            195                 200                 205
Asn Phe Tyr Gln Thr Val Asp Pro Glu Val Ala Lys Leu Phe His Ile
210                 215                 220
Glu Ala Ser Ala Lys Arg Pro Ala Leu Val Leu Leu Lys Lys Glu Ala
225                 230                 235                 240
Glu Lys Leu Asn Arg Phe Asp Gly Glu Phe Ser Lys Ser Ala Ile Ala
                245                 250                 255
Glu Phe Val Phe Ala Asn Lys Leu Pro Leu Val Thr Lys Phe Thr Arg
            260                 265                 270
Glu Ser Ala Pro Leu Ile Phe Glu Ser Ser Ile Lys Lys Gln Leu Ile
            275                 280                 285
Leu Phe Ala Ile Ser Asn Asp Ser Glu Lys Leu Ile Pro Ile Phe Glu
            290                 295                 300
Glu Ser Ser Lys Ser Phe Lys Gly Lys Leu Ile Phe Val Tyr Val Glu
305                 310                 315                 320
Ile Asp Asn Glu Asp Val Gly Lys Pro Val Ser Glu Tyr Phe Gly Ile
                325                 330                 335
Ser Gly Asn Gly Pro Glu Val Leu Gly Tyr Thr Gly Asn Glu Asp Ser
            340                 345                 350
Lys Lys Phe Val Leu Ala Lys Glu Val Thr Leu Asp Asn Ile Lys Ala
            355                 360                 365
Phe Gly Glu Asn Phe Leu Glu Asp Lys Leu Lys Pro Phe Tyr Lys Ser
            370                 375                 380
Asp Pro Ile Pro Glu Thr Asn Asp Gly Asp Val Lys Val Val Gly
385                 390                 395                 400
Asp Asn Phe Asp Asn Ile Val Leu Asp Glu Ser Lys Asp Val Leu Leu
                405                 410                 415
Glu Ile Tyr Ala Pro Trp Cys Gly His Cys Gln Ala Leu Glu Pro Thr
            420                 425                 430
Tyr Asn Lys Leu Ala Lys His Leu Arg Gly Ile Asp Ser Leu Val Ile
            435                 440                 445
Ala Lys Met Asp Gly Thr Thr Asn Glu His Pro Arg Ala Lys Ser Asp
450                 455                 460
Gly Phe Pro Thr Ile Leu Phe Phe Pro Ala Gly Asn Lys Ser Phe Asp
465                 470                 475                 480
Pro Ile Thr Val Asp Thr Asp Arg Thr Val Val Ala Leu Tyr Lys Phe
                485                 490                 495
Ile Lys Lys Asn Ala Ser Ile Pro Phe Lys Leu Gln Lys Pro Val Ser
                500                 505                 510
Ser Pro Lys Ala Val Ser Ser Glu Ala Lys Ser Gly Asp Ala Lys Glu
            515                 520                 525
Ser Pro Lys Ser Ser Thr Thr Asp Val Lys Asp Glu Leu
            530                 535                 540
```

<210> SEQ ID NO 9
<211> LENGTH: 2031
<212> TYPE: DNA
<213> ORGANISM: Zea mays

<400> SEQUENCE: 9

| | | | | | |
|---|---|---|---|---|---|
| ctcaccagct | gcccgcgcat | ccaattcctc | tcgctggacg | gctgcagcac | atcatcaggt | 60 |
| gagaccgtga | gagggaatgg | gatcaacaac | aatgtcccct | ccatcttttc | ccgtcgtcct | 120 |
| cctgctcctc | ctcctcgcca | ccatagccgc | agccgccgga | agcaacatgg | atgaggaggt | 180 |
| ggtggacgac | ctccagtatc | ttattgacaa | ctccgacgac | atccccacca | acgatcccga | 240 |
| cgggtggcct | gagggagact | acgacgacga | cgaccttctc | ttccaagatc | aggaccagga | 300 |
| cctcacaggc | caccagccgg | agatcgacga | gacccacgta | gtggtcctcg | ccgccgcaaa | 360 |
| cttttcctcc | ttcctcgcct | ccagccacca | tgttatggtt | gagttctacg | caccttggtg | 420 |
| tggccactgc | caggagctcg | ccccgggatt | aagccggcgc | cgcgcgcatc | tcgccggctc | 480 |
| aaccaaccaa | ccaaggccca | acttcgccct | gccaaggtc | gacgccaccg | aggaaaccga | 540 |
| cctcgcccag | aagtacgacg | tccagggctt | ccccaccatc | ctcttcttca | tcgatggcgt | 600 |
| ccccagaggc | tataacggag | ccaggaccaa | ggaagccatc | gtcgactgga | tcaacaagaa | 660 |
| gctcggccca | gccgtgcaaa | atgtcaccag | cgtcgacgag | gcccagagca | tactcaccgg | 720 |
| agatgacaaa | gccgtccttg | ccttcctcga | cacactatcc | ggtgctcaca | gtgatgagct | 780 |
| tgctgctgct | tcgaggctgg | aagatagcat | caacttttat | cagacttcga | ctcctgatgt | 840 |
| tgctaagctt | ttccatatcg | atgcagcagc | gaagcgtcca | tccgtagtgc | tgctgaagaa | 900 |
| agaggaggag | aagttgacct | tctatgatgg | ggagtttaaa | gcatcagcca | ttgctggttt | 960 |
| tgtgtctgct | aacaagcttc | ctttggtgac | cacactaact | caagaaactt | ccccttctat | 1020 |
| ttttggcaat | ccaatcaaga | agcagatttt | actatttgct | gttgcaagcg | agtccaccaa | 1080 |
| atttctgccc | atctttaagg | aagcagcaaa | accatttaag | ggaaagttat | tatttgtctt | 1140 |
| tgtgaacga | gacagtgagg | aagttggtga | accagttgcc | gactactttg | gtattactgg | 1200 |
| acaagagacc | acagttcttg | cttacactgg | taatgaagat | gctaggaaat | tttttcttga | 1260 |
| tggtgaggtg | tcacttgaag | ctataaagga | cttcgctgaa | ggtttcttgg | aagacaagct | 1320 |
| tacaccattc | tacaaatcgg | aaccagtgcc | tgaatctaat | gatggggatg | tgaaaattgt | 1380 |
| tgttgggaag | aatctggatc | taatagtttt | tgatgaaaca | aaagatgtac | ttcttgagat | 1440 |
| atatgcacca | tggtgtggtc | attgtcaatc | gctggaacct | acttacaaca | atctagccaa | 1500 |
| gcatctacgt | agtgttgact | cccttgtggt | agccaaaatg | gatggtacta | ccaatgagca | 1560 |
| tccacgtgca | aagtctgacg | gatacccgac | gattctcttc | tatccagctg | ggaagaaaag | 1620 |
| ctttgagcca | atcacttttg | aggggagcg | gacagtggta | gatctgtaca | agttcatcaa | 1680 |
| gaaacatgct | agcatcccctt | tcaagttgaa | gcgccaggag | tcgagaaccg | agagcactcg | 1740 |
| ggcggagggt | gtgaagagct | ctggtacgaa | ctcaaaggac | gaactgtaaa | gagctcaggg | 1800 |
| ttggatgtgt | gttggagtgg | atcagggtga | aagtttccat | ctcaatacaa | gtagatcgat | 1860 |
| cttggtggat | gcgagtgcag | tgttggcctg | agggaggagc | agcagagatg | agtgcttact | 1920 |
| gcttagagag | aggaatgaaa | tcagcaacta | atcaaataaa | atcaaattcc | attaaaaaaa | 1980 |
| aaaaaaaaa | taaaaaaaaa | aaaattaaaa | aaaaataaaa | aaaaaaaaaa | a | 2031 |

<210> SEQ ID NO 10

-continued

<211> LENGTH: 570
<212> TYPE: PRT
<213> ORGANISM: Zea mays

<400> SEQUENCE: 10

```
Met Gly Ser Thr Thr Met Ser Pro Pro Ser Phe Pro Val Val Leu Leu
 1               5                  10                  15

Leu Leu Leu Leu Ala Thr Ile Ala Ala Ala Gly Ser Asn Met Asp
            20                  25                  30

Glu Glu Val Val Asp Asp Leu Gln Tyr Leu Ile Asp Asn Ser Asp Asp
            35                  40                  45

Ile Pro Thr Asn Asp Pro Asp Gly Trp Pro Glu Gly Asp Tyr Asp Asp
     50                  55                  60

Asp Asp Leu Leu Phe Gln Asp Gln Asp Gln Asp Leu Thr Gly His Gln
 65                  70                  75                  80

Pro Glu Ile Asp Glu Thr His Val Val Leu Ala Ala Asn Phe
                 85                  90                  95

Ser Ser Phe Leu Ala Ser Ser His His Val Met Val Glu Phe Tyr Ala
                100                 105                 110

Pro Trp Cys Gly His Cys Gln Glu Leu Ala Pro Gly Leu Ser Arg Arg
                115                 120                 125

Arg Ala His Leu Ala Gly Ser Thr Asn Gln Pro Arg Pro Asn Phe Ala
130                 135                 140

Leu Ala Lys Val Asp Ala Thr Glu Glu Thr Asp Leu Ala Gln Lys Tyr
145                 150                 155                 160

Asp Val Gln Gly Phe Pro Thr Ile Leu Phe Phe Ile Asp Gly Val Pro
                165                 170                 175

Arg Gly Tyr Asn Gly Ala Arg Thr Lys Glu Ala Ile Val Asp Trp Ile
                180                 185                 190

Asn Lys Lys Leu Gly Pro Ala Val Gln Asn Val Thr Ser Val Asp Glu
                195                 200                 205

Ala Gln Ser Ile Leu Thr Gly Asp Asp Lys Ala Val Leu Ala Phe Leu
                210                 215                 220

Asp Thr Leu Ser Gly Ala His Ser Asp Glu Leu Ala Ala Ala Ser Arg
225                 230                 235                 240

Leu Glu Asp Ser Ile Asn Phe Tyr Gln Thr Ser Thr Pro Asp Val Ala
                245                 250                 255

Lys Leu Phe His Ile Asp Ala Ala Lys Arg Pro Ser Val Val Leu
                260                 265                 270

Leu Lys Lys Glu Glu Lys Leu Thr Phe Tyr Asp Gly Glu Phe Lys
                275                 280                 285

Ala Ser Ala Ile Ala Gly Phe Val Ser Ala Asn Lys Leu Pro Leu Val
                290                 295                 300

Thr Thr Leu Thr Gln Glu Thr Ser Pro Ser Ile Phe Gly Asn Pro Ile
305                 310                 315                 320

Lys Lys Gln Ile Leu Leu Phe Ala Val Ala Ser Glu Ser Thr Lys Phe
                325                 330                 335

Leu Pro Ile Phe Lys Glu Ala Ala Lys Pro Phe Lys Gly Lys Leu Leu
                340                 345                 350

Phe Val Phe Val Glu Arg Asp Ser Glu Glu Val Gly Glu Pro Val Ala
                355                 360                 365

Asp Tyr Phe Gly Ile Thr Gly Gln Glu Thr Thr Val Leu Ala Tyr Thr
                370                 375                 380

Gly Asn Glu Asp Ala Arg Lys Phe Phe Leu Asp Gly Glu Val Ser Leu
```

|   |   |   | 385 |   |   |   | 390 |   |   |   | 395 |   |   |   | 400 |
|---|---|---|---|---|---|---|---|---|---|---|---|---|---|---|---|

Glu Ala Ile Lys Asp Phe Ala Glu Gly Phe Leu Glu Asp Lys Leu Thr
                405                 410                 415

Pro Phe Tyr Lys Ser Glu Pro Val Pro Glu Ser Asn Asp Gly Asp Val
            420                 425                 430

Lys Ile Val Val Gly Lys Asn Leu Asp Leu Ile Val Phe Asp Glu Thr
            435                 440                 445

Lys Asp Val Leu Leu Glu Ile Tyr Ala Pro Trp Cys Gly His Cys Gln
        450                 455                 460

Ser Leu Glu Pro Thr Tyr Asn Asn Leu Ala Lys His Leu Arg Ser Val
465                 470                 475                 480

Asp Ser Leu Val Val Ala Lys Met Asp Gly Thr Thr Asn Glu His Pro
                485                 490                 495

Arg Ala Lys Ser Asp Gly Tyr Pro Thr Ile Leu Phe Tyr Pro Ala Gly
            500                 505                 510

Lys Lys Ser Phe Glu Pro Ile Thr Phe Glu Gly Glu Arg Thr Val Val
            515                 520                 525

Asp Leu Tyr Lys Phe Ile Lys Lys His Ala Ser Ile Pro Phe Lys Leu
        530                 535                 540

Lys Arg Gln Glu Ser Arg Thr Glu Ser Thr Arg Ala Glu Gly Val Lys
545                 550                 555                 560

Ser Ser Gly Thr Asn Ser Lys Asp Glu Leu
                565                 570

<210> SEQ ID NO 11
<211> LENGTH: 891
<212> TYPE: DNA
<213> ORGANISM: Zea mays

<400> SEQUENCE: 11

| gcacgagtgg aaatggataa cgaagatgtt ggaaagcctg tttcagaata ctttggtatc | 60 |
|---|---|
| agtgggaatg ctccaaaagt acttggatac actgggaatg atgatggaaa aaaatttgtg | 120 |
| cttgatggag aggtgactac tgacaaaatt aaggcatttg ggaagatttt cgttgaagac | 180 |
| aagctaaaac ttttttacaa gtcagatcca gttcctgaaa gtaatgatgg tgatgtgaaa | 240 |
| atagtagttg gtaataattt tgatgaaatt gtcttggatg agtcaaagga tgttctcctc | 300 |
| gagatttatg ctccctggtg tggccattgc caatcactgg agccaatata caacaagctt | 360 |
| gcaaaacatc ttcgcaatat tgattctctt gtaatagcca agatggatgg aacaacaaat | 420 |
| gagcatccca gggctaagcc tgatggattc cccactcttc tcttcttccc ggcaggaaac | 480 |
| aagagttttg accctattac tgttgataca gatcgtacag tggtagcctt ctacaagttc | 540 |
| ctcaagaaac atgcatcaat cccattcaag ctccagaaac aacctcaac ttctgaatcc | 600 |
| gattccaagg ggagctctga tgccaaagag agccagagta gtgatgtgaa ggacgaatta | 660 |
| tgaggagtta agtgatatat ttttatttat agaaactatg attcagacag atgatgacat | 720 |
| agtgactgag gtaaaaaata ccaagttact tctcacccct ggtcaataaa aaacaaacgg | 780 |
| ggagtggggg gagagagaca aatgcgaggc acacatgtat tactattaac ttcaatttgt | 840 |
| acaacagtgg gtaatttaga attttgattt tgggttgaga cttcaaaaaa a | 891 |

<210> SEQ ID NO 12
<211> LENGTH: 220
<212> TYPE: PRT
<213> ORGANISM: Zea mays

```
<400> SEQUENCE: 12

Ala Arg Val Glu Met Asp Asn Glu Asp Val Gly Lys Pro Val Ser Glu
 1               5                  10                  15

Tyr Phe Gly Ile Ser Gly Asn Ala Pro Lys Val Leu Gly Tyr Thr Gly
                20                  25                  30

Asn Asp Asp Gly Lys Lys Phe Val Leu Asp Gly Glu Val Thr Thr Asp
            35                  40                  45

Lys Ile Lys Ala Phe Gly Glu Asp Phe Val Glu Asp Lys Leu Lys Pro
    50                  55                  60

Phe Tyr Lys Ser Asp Pro Val Pro Glu Ser Asn Asp Gly Asp Val Lys
65                  70                  75                  80

Ile Val Val Gly Asn Asn Phe Asp Glu Ile Val Leu Asp Glu Ser Lys
                85                  90                  95

Asp Val Leu Leu Glu Ile Tyr Ala Pro Trp Cys Gly His Cys Gln Ser
            100                 105                 110

Leu Glu Pro Ile Tyr Asn Lys Leu Ala Lys His Leu Arg Asn Ile Asp
        115                 120                 125

Ser Leu Val Ile Ala Lys Met Asp Gly Thr Thr Asn Glu His Pro Arg
130                 135                 140

Ala Lys Pro Asp Gly Phe Pro Thr Leu Leu Phe Phe Pro Ala Gly Asn
145                 150                 155                 160

Lys Ser Phe Asp Pro Ile Thr Val Asp Thr Asp Arg Thr Val Val Ala
                165                 170                 175

Phe Tyr Lys Phe Leu Lys Lys His Ala Ser Ile Pro Phe Lys Leu Gln
            180                 185                 190

Lys Pro Thr Ser Thr Ser Glu Ser Asp Ser Lys Gly Ser Ser Asp Ala
        195                 200                 205

Lys Glu Ser Gln Ser Ser Asp Val Lys Asp Glu Leu
    210                 215                 220

<210> SEQ ID NO 13
<211> LENGTH: 1126
<212> TYPE: DNA
<213> ORGANISM: Glycine max

<400> SEQUENCE: 13
gcacgagcaa gtttccatta gttacaaagc tgactgaaat gaattctatc agagtctact      60
ccagccccat caagcttcag gttttagtct ttgcaaacat tgatgacttc aagaatcttc     120
ttgaaactct tcaagatgtt gcaaaaacat tcaagtcaaa gataatgttt atatatgtgg     180
atattaatga tgagaacctt gcaaagccct tcttaacatt gtttggtctt gaagaatcaa     240
aaaatactgt ggtcgccgca tttgataatg caatgagctc aaaatatttg ttggagacaa     300
aaccaacaca aagcaatatt gaagagttct gcaataacct tgtgcaaggg tctttgtcac     360
cttacttcaa gtcacagcca attccagata atacagaatc aagtgtccat gttattgtcg     420
ggaaaacatt tgatgatgaa atcttgagca gcgagaagga tgtgctcttg gaggtattta     480
cgccttggtg catcaactgt gaggccacta gcaagcaagt agagaagttg gcaaagcact     540
acaaaggatc aagtaatcta atatttgcaa ggatagatgc ttcagcaaat gaacatccaa     600
aactgcaagt gaatgactac cccacgcttc tactttacag agcagacgat aaggcaaatc     660
cgatcaaact ttccacaaaa tctagtttga agagttggc tgcatccatt aacaaatatg     720
taaaagtcaa gatcaagtc gtcaaagatg agttatagaa catatcaaaa gttttgggga     780 gaaaacact taaccatgaa gaaagtaaaa cattatggaa agaaacaaat attatgttgt     840
```

```
cttgcgtaag cattttctaa tttttattaa cctttcccct gccatttat ggtggtccaa    900 atatgagtta gtctattatt atttgagtta gcttactgct aaattgcgaa agctagtcaa    960
attataacat gtaatgaact acagaacata cttgatacac caaacattgt accgatcaac   1020
actttccatt tgcatctcat agaaacctgc aaatcacagg cttaaagttg atgcattgac   1080
acatatcaaa ctcaagcttt tataattcga aaaaaaaaaa aaaaaa                  1126
```

<210> SEQ ID NO 14
<211> LENGTH: 251
<212> TYPE: PRT
<213> ORGANISM: Glycine max

<400> SEQUENCE: 14

```
Thr Ser Lys Phe Pro Leu Val Thr Lys Leu Thr Glu Met Asn Ser Ile
  1               5                  10                  15

Arg Val Tyr Ser Ser Pro Ile Lys Leu Gln Val Leu Val Phe Ala Asn
             20                  25                  30

Ile Asp Asp Phe Lys Asn Leu Leu Glu Thr Leu Gln Asp Val Ala Lys
         35                  40                  45

Thr Phe Lys Ser Lys Ile Met Phe Ile Tyr Val Asp Ile Asn Asp Glu
     50                  55                  60

Asn Leu Ala Lys Pro Phe Leu Thr Leu Phe Gly Leu Glu Glu Ser Lys
 65                  70                  75                  80

Asn Thr Val Val Ala Ala Phe Asp Asn Ala Met Ser Ser Lys Tyr Leu
                 85                  90                  95

Leu Glu Thr Lys Pro Thr Gln Ser Asn Ile Glu Glu Phe Cys Asn Asn
            100                 105                 110

Leu Val Gln Gly Ser Leu Ser Pro Tyr Phe Lys Ser Gln Pro Ile Pro
        115                 120                 125

Asp Asn Thr Glu Ser Ser Val His Val Ile Val Gly Lys Thr Phe Asp
    130                 135                 140

Asp Glu Ile Leu Ser Ser Glu Lys Asp Val Leu Leu Glu Val Phe Thr
145                 150                 155                 160

Pro Trp Cys Ile Asn Cys Glu Ala Thr Ser Lys Gln Val Glu Lys Leu
                165                 170                 175

Ala Lys His Tyr Lys Gly Ser Ser Asn Leu Ile Phe Ala Arg Ile Asp
            180                 185                 190

Ala Ser Ala Asn Glu His Pro Lys Leu Gln Val Asn Asp Tyr Pro Thr
        195                 200                 205

Leu Leu Leu Tyr Arg Ala Asp Asp Lys Ala Asn Pro Ile Lys Leu Ser
    210                 215                 220

Thr Lys Ser Ser Leu Lys Glu Leu Ala Ala Ser Ile Asn Lys Tyr Val
225                 230                 235                 240

Lys Val Lys Asn Gln Val Val Lys Asp Glu Leu
                245                 250
```

<210> SEQ ID NO 15
<211> LENGTH: 1943
<212> TYPE: DNA
<213> ORGANISM: Glycine max

<400> SEQUENCE: 15

```
gttctcttca ctctcacaat gcgaatcctc gttgtgctct ctctcgccac cctcctcctc     60
ttctcctccc tctttctcac cctctgcgac gacctcaccg acgacgagga cctcggcttc    120
```

-continued

```
ctcgacgagc cctccgccgc gccggagcac ggccactacc acgacgatga cgccaatttc      180
ggcgacttcg aggaggaccc ggaggcgtac aagcagcccg aggtggacga aaggacgtc       240
gtcattttga aggagaagaa cttcaccgac accgtcaaga gcaaccgctt cgtcatggtc      300
gagttctacg cgccctggtg cggccactgc caggccctcg cgccggagta cgccgccgcc      360
gcgacggaac tcaagggcga agacgtaatt ttggcaaagg tggatgccac cgaggagaat      420
gaattggcgc agcagtacga tgttcagggt ttccccactg tccacttctt cgttgatggc      480
attcacaagc cttataatgg ccaaaggacc aaagatgcta tagtgacgtg gataggaaag      540
aagatcggac ctggcatata caacttgact acagtggagg atgctcaacg catcttgacc      600
aacgaaacta agttgttttt gggcttcctc aactctttag ttggtcctga gagtgaggag      660
cttgctgctg cttcaagact tgaggatgat gtcaatttt atcaaactgt ggatcctgat       720
gtggcaaagc ttttccatat tgacccagat gttaagcgcc cagctttgat cctcgtcaag      780
aaagaggagg aaaaacttaa ccactttgat ggcaaatttg agaagtcgga aatagcagac      840
tttgtcttct ccaacaagct tcctttggta acaattttta caagagaaag tgccccatca      900
gtcttcgaaa atccaatcaa gaaacagttg ttgctgtttg caacttcaaa tgattcagag      960
aagttgatcc ctgcatttaa agaagctgca aaatctttca agggaaagtt gatctttgta      1020
tatgtggaaa tggataacga agatgttgga aagcctgttt cagaatactt tggtatcagt      1080
gggaatgctc caaaagtact tgggtacact gggaatgatg atggaaaaaa atttgtgctt      1140
gatggagagg tgactgctga caaaattaag gcatttgggg acgatttcct tgaagacaag      1200
ctaaaacctt tttacaagtc agatccagtt cctgaaagta atgatggtga tgtgaaaata      1260
gtagttggga ataattttga tgaaattgtc ttggatgagt caaggatgt tctcctcgag       1320
atttatgctc cctggtgtgg ccattgccaa gcactggagc caatatacga caagcttgca      1380
aaacatcttc gtaatattga gtctcttgta atagccaaga tggatggaac aacaaatgag      1440
catcccaggg ctaagcctga tggatttccc actctcctct tcttcccggc aggaaacaag      1500
agtttgacc ctattactgt tgatacagat cgtacagtgg tagccttcta caagttcctc       1560
aagaaacatg catcaatccc attcaagctc cagaaaccaa cctcaacttc tgatgccaag      1620
gggagctctg atgccaaaga gagccagagt agtgatgtga aggatgaatt atgaggagtt      1680
aagtgatata tttttattta ttgaaactga ttcagacaga tgatgacatg gtgactgagg      1740
gagaaaatac caagctgctt ctctccccta gccaataaaa acaaacgagg agtgggggga      1800
aggagacaaa tgcgaggcac atatgtatta ctattaactt aaattttac aactgggcat       1860
tttagaattt tgggttgaga cttcaataaa ttccccctta aatttaaaa aaaaaaaaaa       1920
aaaaaaaaac tcgagactag ttc                                             1943
```

<210> SEQ ID NO 16
<211> LENGTH: 551
<212> TYPE: PRT
<213> ORGANISM: Glycine max

<400> SEQUENCE: 16

Met Arg Ile Leu Val Val Leu Ser Leu Ala Thr Leu Leu Phe Ser
1               5                   10                  15

Ser Leu Phe Leu Thr Leu Cys Asp Asp Leu Thr Asp Asp Glu Asp Leu
                20                  25                  30

Gly Phe Leu Asp Glu Pro Ser Ala Ala Pro Glu His Gly His Tyr His
        35                  40                  45

-continued

```
Asp Asp Asp Ala Asn Phe Gly Asp Phe Glu Glu Asp Pro Glu Ala Tyr
 50              55                  60
Lys Gln Pro Glu Val Asp Glu Lys Asp Val Val Ile Leu Lys Glu Lys
 65              70                  75                  80
Asn Phe Thr Asp Thr Val Lys Ser Asn Arg Phe Val Met Val Glu Phe
             85                  90                  95
Tyr Ala Pro Trp Cys Gly His Cys Gln Ala Leu Ala Pro Glu Tyr Ala
             100                 105                 110
Ala Ala Ala Thr Glu Leu Lys Gly Glu Asp Val Ile Leu Ala Lys Val
         115                 120                 125
Asp Ala Thr Glu Glu Asn Glu Leu Ala Gln Gln Tyr Asp Val Gln Gly
 130                 135                 140
Phe Pro Thr Val His Phe Val Asp Gly Ile His Lys Pro Tyr Asn
145                 150                 155                 160
Gly Gln Arg Thr Lys Asp Ala Ile Val Thr Trp Ile Gly Lys Lys Ile
             165                 170                 175
Gly Pro Gly Ile Tyr Asn Leu Thr Thr Val Glu Asp Ala Gln Arg Ile
             180                 185                 190
Leu Thr Asn Glu Thr Lys Val Val Leu Gly Phe Leu Asn Ser Leu Val
         195                 200                 205
Gly Pro Glu Ser Glu Glu Leu Ala Ala Ala Ser Arg Leu Glu Asp Asp
 210                 215                 220
Val Asn Phe Tyr Gln Thr Val Asp Pro Asp Val Ala Lys Leu Phe His
225                 230                 235                 240
Ile Asp Pro Asp Val Lys Arg Pro Ala Leu Ile Leu Val Lys Lys Glu
             245                 250                 255
Glu Glu Lys Leu Asn His Phe Asp Gly Lys Phe Glu Lys Ser Glu Ile
             260                 265                 270
Ala Asp Phe Val Phe Ser Asn Lys Leu Pro Leu Val Thr Ile Phe Thr
         275                 280                 285
Arg Glu Ser Ala Pro Ser Val Phe Glu Asn Pro Ile Lys Lys Gln Leu
 290                 295                 300
Leu Leu Phe Ala Thr Ser Asn Asp Ser Glu Lys Leu Ile Pro Ala Phe
305                 310                 315                 320
Lys Glu Ala Ala Lys Ser Phe Lys Gly Lys Leu Ile Phe Val Tyr Val
             325                 330                 335
Glu Met Asp Asn Glu Asp Val Gly Lys Pro Val Ser Glu Tyr Phe Gly
             340                 345                 350
Ile Ser Gly Asn Ala Pro Lys Val Leu Gly Tyr Thr Gly Asn Asp Asp
         355                 360                 365
Gly Lys Lys Phe Val Leu Asp Gly Glu Val Thr Ala Asp Lys Ile Lys
 370                 375                 380
Ala Phe Gly Asp Asp Phe Leu Glu Asp Lys Leu Lys Pro Phe Tyr Lys
385                 390                 395                 400
Ser Asp Pro Val Pro Glu Ser Asn Asp Gly Asp Val Lys Ile Val Val
             405                 410                 415
Gly Asn Asn Phe Asp Glu Ile Val Leu Asp Glu Ser Lys Asp Val Leu
             420                 425                 430
Leu Glu Ile Tyr Ala Pro Trp Cys Gly His Cys Gln Ala Leu Glu Pro
         435                 440                 445
Ile Tyr Asp Lys Leu Ala Lys His Leu Arg Asn Ile Glu Ser Leu Val
 450                 455                 460
Ile Ala Lys Met Asp Gly Thr Thr Asn Glu His Pro Arg Ala Lys Pro
```

```
                465                 470                 475                 480
Asp Gly Phe Pro Thr Leu Leu Phe Phe Pro Ala Gly Asn Lys Ser Phe
                    485                 490                 495
Asp Pro Ile Thr Val Asp Thr Asp Arg Thr Val Val Ala Phe Tyr Lys
                500                 505                 510
Phe Leu Lys Lys His Ala Ser Ile Pro Phe Lys Leu Gln Lys Pro Thr
            515                 520                 525
Ser Thr Ser Asp Ala Lys Gly Ser Ser Asp Ala Lys Glu Ser Gln Ser
        530                 535                 540
Ser Asp Val Lys Asp Glu Leu
545                 550

<210> SEQ ID NO 17
<211> LENGTH: 1565
<212> TYPE: DNA
<213> ORGANISM: Triticum aestivum

<400> SEQUENCE: 17
```

| | | | | | |
|---|---|---|---|---|---|
| gcacgagacc | acgcggagct | gctgctgctc | gggtacgcgc | cgtggtgtga | gcgcagcgcg | 60 |
| cagctcatgc | cgcggttcgc | cgaggccgcc | gccgcgctgc | gcgccatggg | cagcgccgtc | 120 |
| gccttcgcga | agctcgacgg | ggagcgctac | cccaaggcgg | ctgccgccgt | cggggtcaag | 180 |
| ggcttccccca | ccgtgctcct | cttcgtcaat | ggcaccgagc | acgcctacca | tggcctccac | 240 |
| accaaggacg | ccatagttac | ttgggtaaga | agaaaactg | gcgagccaat | cattaggctt | 300 |
| cagtctaagg | attcagctga | ggagttcctc | aaaaaggaca | tgacctttgt | tattgggcta | 360 |
| ttcaagaatt | ttgagggagc | agaccatgaa | gaatttgtga | aggcagcaac | cacagacaac | 420 |
| gaggtacagt | ttgtagaaac | cagtgataca | cgtgttgcca | agttctatt | tccaggtatt | 480 |
| acgtccgagg | agaaatttgt | gggcctcgtt | aaaagcgagc | cagagaagtt | tgaaaagttc | 540 |
| gatgggaaat | ttgaagaaac | ggaaattctg | cggtttgtgg | agctcaacaa | gtttcctcta | 600 |
| attactgtat | tcactgagct | caattccggt | aaagtatatt | caagccctat | taagctacag | 660 |
| gtcttcaccct | ttgcagaggc | ttatgatttt | gaagatctgg | aatctatggt | tgaagaaata | 720 |
| gccagagcat | tcaagacaaa | gataatgttt | atatatgttg | acactgctga | gaaaaccttt | 780 |
| gcaaaccat | tcctcactct | ttatggcctt | gaatcagaaa | aaaagcctac | tgttacagca | 840 |
| tttgatacaa | gcaatggagc | caagtatctg | atggaggcag | atatcaatgc | aaacaacctg | 900 |
| agggagttct | gcttaagtct | tctggatggc | acgctcccgc | cataccacaa | atcagaacca | 960 |
| ttgcctcaag | agaagggact | tattgaaaag | gttgttggtc | gtacatttga | ttcttctgtg | 1020 |
| ctggaaagtc | atcaaaacgt | cttccttgag | gttcatacac | cttggtgtgt | tgactgtgaa | 1080 |
| gcgataagta | aaaatgttga | gaagttggcg | aagcatttca | gtggttcgga | caatcttaaa | 1140 |
| tttgcacgca | tagatgcttc | tgtgaatgaa | catcccaaat | tgaaggtgaa | taattccccg | 1200 |
| acgctattcc | tttatcttgc | tgaagacaaa | acaacccga | tcaagctttc | aaagaaatcg | 1260 |
| agtgtcaagg | acatggccaa | actgatcaag | gagaagctgc | aaataccaga | cgtggagaca | 1320 |
| gtagcggccc | ctgacaacgt | caaggatgag | ctataacctg | tagtagacaa | actaaggtcc | 1380 |
| agtgaaggaa | aaattgcagc | atgtttgcgt | gttttgcccc | aacctgatca | cagagctcag | 1440 |
| ctttattcgc | gtgctgtgtt | aagttgacta | aagtcaatgg | tatataatat | aggtacctaa | 1500 |
| atcaaagagg | cttcggcccc | taaaaaaaaa | aaaaaaaaaa | aaaaaaaaaa | aaaaaaaaaa | 1560 |
| aaaaa | | | | | | 1565 |

<210> SEQ ID NO 18
<211> LENGTH: 451
<212> TYPE: PRT
<213> ORGANISM: Triticum aestivum

<400> SEQUENCE: 18

```
Ala Arg Asp His Ala Glu Leu Leu Leu Gly Tyr Ala Pro Trp Cys
 1               5                  10                  15

Glu Arg Ser Ala Gln Leu Met Pro Arg Phe Ala Glu Ala Ala Ala
                20                  25                  30

Leu Arg Ala Met Gly Ser Ala Val Ala Phe Ala Lys Leu Asp Gly Glu
            35                  40                  45

Arg Tyr Pro Lys Ala Ala Ala Val Gly Val Lys Gly Phe Pro Thr
        50                  55                  60

Val Leu Leu Phe Val Asn Gly Thr Glu His Ala Tyr His Gly Leu His
 65                  70                  75                  80

Thr Lys Asp Ala Ile Val Thr Trp Val Arg Lys Lys Thr Gly Glu Pro
                85                  90                  95

Ile Ile Arg Leu Gln Ser Lys Asp Ser Ala Glu Glu Phe Leu Lys Lys
                100                 105                 110

Asp Met Thr Phe Val Ile Gly Leu Phe Lys Asn Phe Glu Gly Ala Asp
            115                 120                 125

His Glu Glu Phe Val Lys Ala Ala Thr Thr Asp Asn Glu Val Gln Phe
        130                 135                 140

Val Glu Thr Ser Asp Thr Arg Val Ala Lys Val Leu Phe Pro Gly Ile
145                 150                 155                 160

Thr Ser Glu Glu Lys Phe Val Gly Leu Val Lys Ser Glu Pro Glu Lys
                165                 170                 175

Phe Glu Lys Phe Asp Gly Lys Phe Glu Glu Thr Glu Ile Leu Arg Phe
            180                 185                 190

Val Glu Leu Asn Lys Phe Pro Leu Ile Thr Val Phe Thr Glu Leu Asn
        195                 200                 205

Ser Gly Lys Val Tyr Ser Ser Pro Ile Lys Leu Gln Val Phe Thr Phe
    210                 215                 220

Ala Glu Ala Tyr Asp Phe Glu Asp Leu Glu Ser Met Val Glu Glu Ile
225                 230                 235                 240

Ala Arg Ala Phe Lys Thr Lys Ile Met Phe Ile Tyr Val Asp Thr Ala
                245                 250                 255

Glu Glu Asn Leu Ala Lys Pro Phe Leu Thr Leu Tyr Gly Leu Glu Ser
            260                 265                 270

Glu Lys Lys Pro Thr Val Thr Ala Phe Asp Thr Ser Asn Gly Ala Lys
        275                 280                 285

Tyr Leu Met Glu Ala Asp Ile Asn Ala Asn Leu Arg Glu Phe Cys
    290                 295                 300

Leu Ser Leu Leu Asp Gly Thr Leu Pro Pro Tyr His Lys Ser Glu Pro
305                 310                 315                 320

Leu Pro Gln Glu Lys Gly Leu Ile Glu Lys Val Val Gly Arg Thr Phe
                325                 330                 335

Asp Ser Ser Val Leu Glu Ser His Gln Asn Val Phe Leu Glu Val His
            340                 345                 350

Thr Pro Trp Cys Val Asp Cys Glu Ala Ile Ser Lys Asn Val Glu Lys
        355                 360                 365

Leu Ala Lys His Phe Ser Gly Ser Asp Asn Leu Lys Phe Ala Arg Ile
    370                 375                 380
```

```
Asp Ala Ser Val Asn Glu His Pro Lys Leu Lys Val Asn Asn Ser Pro
385                 390                 395                 400

Thr Leu Phe Leu Tyr Leu Ala Glu Asp Lys Asn Asn Pro Ile Lys Leu
                405                 410                 415

Ser Lys Lys Ser Ser Val Lys Asp Met Ala Lys Leu Ile Lys Glu Lys
                420                 425                 430

Leu Gln Ile Pro Asp Val Glu Thr Val Ala Ala Pro Asp Asn Val Lys
            435                 440                 445

Asp Glu Leu
    450
```

<210> SEQ ID NO 19
<211> LENGTH: 1078
<212> TYPE: DNA
<213> ORGANISM: Triticum aestivum

<400> SEQUENCE: 19

```
gcacgaggtt cagagcatct gcgattgcca agtttgtttc ggccaacaaa atcccattga      60
tcaccaccct cacacaggag accgcccctg cgattttcga taatccgatc aagaagcaaa     120
ttttgctgtt tgctgttgcg aaggagtcct caaaatttct gcccatcatt aaggaaacag     180
caaaatcatt caaggggaag cttttatttg tctttgtgga gcgtgacaat gaggaagttg     240
gcgaacctgt tgccaattac tttggaatta ctggacaaga gaccacggtt cttgcttaca     300
ctgggaatga agacgctaag aagttcttct tcaccggtga atatcactg acaccatta      360
aggaatttgc tcaagatttc atggaggaca agctcacacc atcctacaag tctgacccag     420
tacctgaatc caatgatgag gacgtcaaag ttgttgttgg caagagtcta gatcaaatag     480
ttctggatga gtcaaaggat gtccttttgg agatatatgc gccatggtgt ggccattgtc     540
agtcactgga gcctatctac aacaagctgg ccaagtaccct ccgtggcatc gactcccttg    600
taatagccaa aatggacggc acaaacaatg agcatcctcg tgccaagccc gatgggttcc     660
ccacgatact cttctaccca gctgggaaga aaagctttga gcctataact ttcgagggg      720
gccggacagt ggtagagatg tacaagttcc tcaagaagca tgccgccatc cctttcaagc     780
tcaagcgccc ggactcgtca gcggcacgga ccgacagcgc cgagggccca ggctcgacca     840
ccgacagcga gaagagctcc ggctcgaacc cgaaggacga gttgtagggg attgacaagt     900
acgaggaggc gccgatgatg tcgaaatcag gaggtggaga aggaatggct aagctaggta     960
tcaaccaacc ttggctgctg caagtgtatg ctgacaacac aaatattaac tgctgtagaa    1020
tccaataaaa taaagcaag aggtcctttt tcttagtact aaaaaaaaaa aaaaaaaa      1078
```

<210> SEQ ID NO 20
<211> LENGTH: 294
<212> TYPE: PRT
<213> ORGANISM: Triticum aestivum

<400> SEQUENCE: 20

```
Thr Arg Phe Arg Ala Ser Ala Ile Ala Lys Phe Val Ser Ala Asn Lys
1               5                   10                  15

Ile Pro Leu Ile Thr Thr Leu Thr Gln Glu Thr Ala Pro Ala Ile Phe
            20                  25                  30

Asp Asn Pro Ile Lys Lys Gln Ile Leu Leu Phe Ala Val Ala Lys Glu
        35                  40                  45

Ser Ser Lys Phe Leu Pro Ile Ile Lys Glu Thr Ala Lys Ser Phe Lys
    50                  55                  60
```

-continued

```
Gly Lys Leu Leu Phe Val Phe Val Glu Arg Asp Asn Glu Val Gly
 65              70                  75                  80

Glu Pro Val Ala Asn Tyr Phe Gly Ile Thr Gly Gln Glu Thr Thr Val
             85                  90                  95

Leu Ala Tyr Thr Gly Asn Glu Asp Ala Lys Lys Phe Phe Phe Thr Gly
            100                 105                 110

Glu Ile Ser Leu Asp Thr Ile Lys Glu Phe Ala Gln Asp Phe Met Glu
            115                 120                 125

Asp Lys Leu Thr Pro Ser Tyr Lys Ser Asp Pro Val Pro Glu Ser Asn
            130                 135                 140

Asp Glu Asp Val Lys Val Val Gly Lys Ser Leu Asp Gln Ile Val
145                 150                 155                 160

Leu Asp Glu Ser Lys Asp Val Leu Leu Glu Ile Tyr Ala Pro Trp Cys
                165                 170                 175

Gly His Cys Gln Ser Leu Glu Pro Ile Tyr Asn Lys Leu Ala Lys Tyr
                180                 185                 190

Leu Arg Gly Ile Asp Ser Leu Val Ile Ala Lys Met Asp Gly Thr Asn
        195                 200                 205

Asn Glu His Pro Arg Ala Lys Pro Asp Gly Phe Pro Thr Ile Leu Phe
        210                 215                 220

Tyr Pro Ala Gly Lys Lys Ser Phe Glu Pro Ile Thr Phe Glu Gly Gly
225                 230                 235                 240

Arg Thr Val Val Glu Met Tyr Lys Phe Leu Lys Lys His Ala Ala Ile
                245                 250                 255

Pro Phe Lys Leu Lys Arg Pro Asp Ser Ser Ala Ala Arg Thr Asp Ser
                260                 265                 270

Ala Glu Gly Pro Gly Ser Thr Thr Asp Ser Glu Lys Ser Ser Gly Ser
                275                 280                 285

Asn Pro Lys Asp Glu Leu
                290
```

PLANT PROTEIN DISULFIDE ISOMERASES

This application claims the benefit of U.S. Provisional Application No. 60/104,426, filed Oct. 15, 1998.

FIELD OF THE INVENTION

This invention is in the field of plant molecular biology. More specifically, this invention pertains to nucleic acid fragments encoding protein disulfide isomerases in plants and seeds.

BACKGROUND OF THE INVENTION

Protein folding requires the assistance of folding helpers in vivo. The formation or isomerization of disulfide bonds in proteins is a slow process requiring catalysis. In nascent polypeptide chains the cysteine residues are in the thiol form. The formation of the disulfide bonds usually occurs simultaneously with the folding of the polypeptide, in the endoplasmic reticulum of eukaryotes or in the periplasm of Gram-negative bacteria. Cells contain three types of accessory proteins that function to assist polypeptides in folding to their native conformations: protein disulfide isomerases, propyl cis-trans isomerases, and molecular chaperones.

Protein disulfide isomerase (PDI) is a homodimeric eukaryotic enzyme which catalyzes disulfide interchange reactions. PDI is also thought to be the beta subunit of the heterotetramer prolyl hydrolase, the enzyme that hydroxylates the proline residues in Collagen. PDI appears to belong to a family of closely related proteins which have specific functions. PDI (EC 5.3.4.1), also called S-S rearrangase, catalyzes the rearrangement of both intrachain and interchain disulfide bonds in proteins to form native structures. The reaction depends on sulfhydryl-disulfide interchange, and PDI needs reducing agents or partly-reduced enzyme. A family of PDI-like proteins has been identified in mammals, yeasts, fungi, plants, and Drosophila.

In Drosophila, a PDI precursor was identified by screening a genomic DNA library at reduced stringency hybridization conditions using a rat Phospholipase C alpha cDNA probe. Northern analysis showed that this gene encodes a transcript that is present throughout development, in heads and bodies of adults. The encoded protein contains two domains exhibiting high similarity to thioredoxin, two regions that are similar to the hormone binding domain of human estrogen receptor, and a C-terminal ER-retention signal (KDEL). Overall, this Drosophila PDI gene contains a higher similarity to rat protein disulfide isomerase (53% identical) than to rat Phospholipase C alpha (30% identical) (McKay et al. (1995) *Insect Biochem. Mol. Biol.* 25:647–654).

Another member of the PDI family is ERp60, a PDI isoform initially misidentified as a phosphatidylinositol-specific phospholipase C. The human and Drosophila ERp60 polypeptides have been cloned and expressed. These two ERp60 polypeptides are similar to human PDI within almost all their domains, the only exception being the extreme C-terminal region. Coexpression in insect cells of the human or Drosophila ERp10 with the alpha subunit of human propyl 4-hydrolase does not result in tetramer formation or prolyl 4-hydroxylase activity in the cells. This lack of tetramer formation is not only due to the differences in the C-terminal region since no prolyl 4-hydroxylase tetramer is formed when a human ERp60 hybrid containing the C-terminal region of the human PDI polypeptide is used (Koivunen et al. (1996) *Biochem. J.* 316:599–605). The 5' flanking region of the ERp60 gene has no TATAA box or CCAAT motif but contains several potential binding sites for transcription factors. The highest levels of expression of the human ERp60 mRNA are found in the liver, placenta, lung, pancreas, and kidney, and the lowest in the heart, skeletal muscle, and brain. The ERp60 gene has been mapped by fluorescence in situ hybridization to 15q15, a different chromosome than where the human PDI and thioredoxin genes are found (Koivunen et al. (1997) *Genomics* 42:397–404).

Full-length cDNA clones encoding two members of the mice PDI family have been cloned, sequenced, and expressed (ERp59/PDI and ERp72). ERp59/PDI has been identified as the microsomal PDI. The ERp72 amino acid sequence shares sequence identity with ERp59/PDI at three discrete regions, having three copies of the sequences that are thought to be the CGHC-containing active sites of ERp59/PDI. ERp59/PDI has the sequence Lys-Asp-Glu-Leu at its COOH terminus while ERp72 has the related sequence Lys-Glu-Glu-Leu (Mazzarella et al. (1990) *J. Biol. Chem.* 265:1094–1101). A cDNA clone containing sequence similarity to the mammalian lumenal endoplasmic reticulum protein ERp72 has been isolated from an alfalfa (*Medicago sativa* L.) cDNA library by screening with a cDNA encoding human PDI. The polypeptide encoded by this cDNA possesses a putative N-terminal secretory signal sequence and two regions identical to the active sites of PDI and ERp72. This protein appears to be encoded by a small gene family in alfalfa, whose transcripts are constitutively expressed in all major organs of the plant. In alfalfa cell suspension cultures, ERp72 transcripts are induced by treatment with tunicamycin, but not in response to calcium ionophore, heat shock or fungal elicitor (Shorrosh and Dixon (1992) *Plant J.* 2:51 –58).

Another member of the PDI family is ERp5. The amino acid sequence deduced from this cDNA insert contains two copies of the 11-amino-acid sequence Val-Glu-Phe-Tyr-Ala-Pro-Trp-Cys-Gly-His-Cys. Duplicate copies of this sequence are found in the active sites of rat and human PDI and in Form I phosphoinositide-specific phospholipase C. Genomic sequences similar to the cDNA clone are amplified 10–20-fold in hamster cells selected for resistance to increasing concentrations of hydroxyurea, a phenomenon observed earlier with cDNA clones for the M2 subunit of ribonucleotide reductase and ornithine decarboxylase. RNA blots probed with ERp5 cDNA show two poly(A)+ RNA species which are elevated in hydroxyurea-resistant cells (Chaudhuri et. al. (1992) *Biochem. J.* 281:645–650).

A PDI-like protein from *Acanthamoeba castellanii* contains two highly conserved thioredoxin-like domains, each about 100 amino acids. However, the *A. castellanii* PDI-like protein differs from other members in many aspects, including the overall organization and isoelectric point. Southern and Northern analyses demonstrate that the PDI-like protein is encoded by a single-copy gene which is transcribed to generate a 1500-nucleotide MRNA (Wong and Bateman (1994) *Gene* 150:175–179).

The Chlamydomonas RB60 gene encodes a chloroplast-localized PDI which is involved in the redox-regulated binding of chloroplast poly(A)-binding protein to the 5'-leader region of psbA MRNA. Protein disulfide isomerase RB60 regulates chloroplast translational activation (Kim and Mayfield (1997) *Science* 278:1954–1957).

High level gene expression does not always lead to corresponding high level secretion of heterologous proteins. The rate limiting step has been shown, in many cases, to be the processing and exit of the protein from the endoplasmic reticulum. Proteins or peptides with high levels of disulfide bonds can be adversely affected during expression. Therefore, coexpression and/or overexpression of PDIs could significantly enhance expression levels of many heterologous proteins. An example would be the coexpression of PDIs with insect-selective neurotoxins, since many of these are highly enriched in cysteines and feature multiple disulfide bonds.

Protein disulfide isomerases have been described in alfalfa (2 genes and one probable PDI P5 homolog), barley (2 genes, and one probable PDI PS homolog), maize, wheat, tobacco, and castor bean. In addition, based on sequence similarity to other known PDIs, two putative protein disulfide isomerases have been identified in Arabidopsis. Included in this application are corn, and soybean ESTs with sequence similarities to protein disulfide isomerase precursor. The corn sequences included share no similarity with the known maize PDI. Also included are corn, balsam pear, soybean, and the wheat ESTs with sequence similarities to RB60. Presently there are no plant RB60-homologs in the public domain. Overexpression of any of these PDIs together with another foreign protein will result in an increased yield of secreted, active foreign protein due to proper folding of the foreign protein.

Present in the NCBI database are corn and soybean sequences with similarities to the polynucleotides included in the present application. These ESTs have NCBI General Identifier NOs:4289796, 4827500, 5124153, 5325044, 5361231, 5525515, 5597319, 5650368, 5688597, 5714111, 5770161, and 5804735.

SUMMARY OF THE INVENTION

The present invention relates to isolated polynucleotides comprising a nucleotide sequence encoding a protein disulfide isomerase precursor polypeptide of at least 100 amino acids that has at least 85% identity based on the Clustal method of alignment when compared to a polypeptide selected from the group consisting of a corn protein disulfide isomerase precursor polypeptide selected from the group consisting of SEQ ID NO:2, and SEQ ID NO:6, a soybean protein disulfide isomerase precursor polypeptide of SEQ ID NO:4. The present invention relates to isolated polynucleotides comprising a nucleotide sequence encoding an RB60 polypeptide of at least 100 amino acids that has at least 85% identity based on the Clustal method of alignment when compared to a polypeptide selected from the group consisting of a balsam pear RB60 polypeptide of SEQ ID NO:8, a corn RB60 polypeptide selected from the group consisting of SEQ ID NO:10 and SEQ ID NO:12, a soybean RB60 polypeptide selected from the group consisting of SEQ ID NO:14 and SEQ ID NO:16, and a wheat RB60 polypeptide selected from the group consisting of SEQ ID NO:18 and SEQ ID NO:20. The present invention also relates to an isolated polynucleotide comprising the complement of the nucleotide sequences described above.

It is preferred that the isolated polynucleotides of the claimed invention consist of a nucleic acid sequence selected from the group consisting of SEQ ID NOs:1, 3, 5, 7, 9, 11, 13, 15, 17, and 19 that codes for the polypeptide selected from the group consisting of SEQ ID NOs:2, 4, 6, 8, 10, 12, 14, 16, 18 and 20. The present invention also relates to an isolated polynucleotide comprising a nucleotide sequence of at least 40 (preferably at least 30, most preferably at least 15) contiguous nucleotides derived from a nucleotide sequence selected from the group consisting of SEQ ID NOs:1, 3, 5, 7, 9, 11, 13, 15, 17, and 19 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell or virus. A virus host cell of the present invention is preferably a baculovirus. The baculovirus preferably comprises an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a protein disulfide isomerase precursor or an RB60 polypeptide of at least 100 amino acids comprising at least 85% homology based on the Clustal method of alignment compared to a polypeptide selected from the group consisting of SEQ ID NOs:2, 4, 6, 8, 10, 12, 14, 16, 18, and 20.

The present invention relates to a method of selecting an isolated polynucleotide that affects the level of expression of a protein disulfide isomerase precursor or an RB60 polypeptide in a host cell, the method comprising the steps of:

constructing an isolated polynucleotide of the present invention or an isolated chimeric gene of the present invention;

introducing the isolated polynucleotide or the isolated chimeric gene into a host cell (preferably a plant cell);

measuring the level a protein disulfide isomerase precursor or an RB60 polypeptide in the plant cell containing the isolated polynucleotide; and comparing the level of a protein disulfide isomerase precursor or an RB60 polypeptide in the host cell containing the isolated polynucleotide with the level of a protein disulfide isomerase precursor or an RB60 polypeptide in a host cell that does not contain the isolated polynucleotide.

The present invention relates to a method of obtaining a nucleic acid fragment encoding a substantial portion of a protein disulfide isomerase precursor or an RB60 polypeptide, preferably a plant protein disulfide isomerase precursor or an RB60 polypeptide, comprising the steps of: synthesizing an oligonucleotide primer comprising a nucleotide sequence of at least 40 (preferably at least 30, most preferably at least 15) contiguous nucleotides derived from a nucleotide sequence selected from the group consisting of SEQ ID NOs:1, 3, 5, 7, 9, 11, 13, 15, 17, and 19 and the complement of such nucleotide sequences; and amplifying a nucleic acid fragment (preferably a cDNA inserted in a cloning vector) using the oligonucleotide primer. The amplified nucleic acid fragment preferably will encode a portion of a protein disulfide isomerase precursor or an RB60 amino acid sequence.

The present invention also relates to a method of obtaining a nucleic acid fragment encoding all or a subsantial portion of the amino acid sequence encoding a protein disulfide isomerase precursor or an RB60 polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

BRIEF DESCRIPTION OF THE SEQUENCE LISTING

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Protein Disulfide Isomerases

| | | SEQ ID NO: | |
|---|---|---|---|
| Protein | Clone Designation | (Nucleotide) | (Amino Acid) |
| Corn PDI precursor | cr1n.pk0090.d2 | 1 | 2 |
| Soybean PDI precursor | srr3c.pk002.a8 | 3 | 4 |
| Corn PDI precursor | csi1.pk0032.c9 | 5 | 6 |
| Balsam Pear RB60 | fds.pk0022.c11 | 7 | 8 |
| Corn PDI RB60 | Contig of:<br>cen3n.pk0155.e7<br>cs1.pk0100.a7<br>p0032.crcbb52r<br>p0125.czabp07r | 9 | 10 |
| Corn PDI RB60 | cs1.pk0077.f10 | 11 | 12 |
| Soybean PDI RB60 | sr1.pk0095.e9 | 13 | 14 |
| Soybean PDI RB60 | Contig of:<br>scr1c.pk005.i17<br>sdp2c.pk038.e22<br>sdp3c.pk021.a3<br>sfl1.pk0026.h1<br>sl2.pk0075.b10 | 15 | 16 |
| Wheat PDI RB60 | wl1n.pk0027.f4 | 17 | 18 |
| Wheat PDI RB60 | wre1n.pk0015.d10 | 19 | 20 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, or synthetic DNA. An isolated polynucleotide of the present invention may include at least 40 contiguous nucleotides, preferably at least 30 contiguous nucleotides, most preferably at least 15 contiguous nucleotides, of the nucleic acid sequence of the SEQ ID NOs: 1, 3, 5, 7, 9, 11, 13, 15, 17, or 19.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic acid fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 40 (preferably at least 30, most preferably at least 15) contiguous nucleotides derived from a nucleotide sequence selected from the group consisting of SEQ ID NOs:1, 3, 5, 7, 9, 11, 13, 15, 17, 19 and the complement of such nucleotide sequences may be used in methods of selecting an isolated polynucleotide that affects the expression of a polypeptide (such as PDI precursor or PDI RB60) in a host cell. A method of selecting an isolated polynucleotide that affects the level of expression of a polypeptide in a host cell (eukaryotic, such as plant, or prokarotic such as yeast bacterial or virus) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are 80% identical to the amino acid sequences reported herein. Preferred nucleic acid fragments encode amino acid sequences that are 85% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Suitable nucleic acid fragments not only have the above identities but typically encode a polypeptide having at least 50 amino acids, preferably 100 amino acids, more preferably 150 amino acids, still more preferably 200 amino acids, and most preferably 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or flnctional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) Biochemistry of Plants 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) Mol. Biotechnol. 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) Plant Cell 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the MRNA and so can be translated into a polypeptide by the cell. "Antisense RNA" refers to an RNA transcript that is complementary to all or part of a target primary transcript or MRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several PDIs have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other PDIs, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1 989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 40 (preferably at least 30, most preferably at least 15) contiguous nucleotides derived from a nucleotide sequence selected from the group consisting of SEQ ID NOs:1, 3, 5, 7, 9, 11, 13, 15, 17, 19 and the complement of such nucleotide sequences may be used in such methods to obtain a nucleic acid fragment encoding a substantial portion of an amino acid sequence of a polypeptide (such as PDI precursor or PDI RB 60). The present invention relates to a method of obtaining a nucleic acid fragment encoding a substantial portion of a polypeptide (such as PDI precursor or PDI RB 60) preferably a substantial portion of a polypeptide of a plant gene, comprising the steps of: synthesizing an oligonucleotide primer comprising a nucleotide sequence of at least 40 (preferably at least 30, most preferably at least 15) contiguous nucleotides derived from a nucleotide sequence selected from the group consisting of SEQ ID NOs:1, 3, 5, 7, 9, 11, 13, 15, 17, 19 and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide (such as PDI precursor or PDI RB 60).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher levels than normal or in cell types or developmental stages in which they are not normally found. This would have the effect of altering the level of properly folded proteins in those cells. Coexpression of a member of the PDI family with another foreign protein will result in a greater yield of active, secreted foreign protein due to the improvement in proper folding done by the PDI.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J*. 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded protein disulfide isomerases. An example of a vector for high level expression of the instant polypeptides in a bacterial host is provided (Example 7).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art. Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various balsam pear, corn, rice, soybean and wheat tissues were prepared. The characteristics of the libraries are described below.

TABLE 2 cDNA Libraries from Balsam Pear, Corn, Rice, Soybean and Wheat

| Library | Tissue | Clone |
|---|---|---|
| cen3n | Corn Endosperm 20 Days After Pollination* | cen3n.pk0155.e7 |
| cr1n | Corn Root From 7 Day Old Seedlings* | cr1n.pk0090.d2 |
| cs1 | Corn Leaf Sheath From 5 Week Old Plant | cs1.pk0077.f10 |
| cs1 | Corn Leaf Sheath From 5 Week Old Plant | cs1.pk0100.a7 |
| csi1 | Corn Silk | csi1.pk0032.c9 |
| fds | *Momordica charantia* Developing Seed | fds.pk0022.c11 |
| p0032 | Corn Regenerating Callus (Hi-II 223a and 1129e), 10 and 14 Days After Auxin Removal, Pooled | p0032.crcbb52r |
| p0125 | Corn Anther Prophase I* | p0125.czabp07r |
| scr1c | Soybean Embryogenic Suspension Culture Subjected to 4 Vacuum Cycles and Collected 12 Hours Later | scr1c.pk005.i17 |
| sdp2c | Soybean Developing Pods (6–7 mm) | sdp2c.pk038.e22 |
| sdp3c | Soybean Developing Pods (8–9 mm) | sdp3c.pk021.a3 |
| sfl1 | Soybean Immature Flower | sfl1.pk0026.h1 |
| sl2 | Soybean Two-Week-Old Developing Seedlings Treated With 2.5 ppm chlorimuron | sl2.pk0075.b10 |
| sr1 | Soybean Root | sr1.pk0095.e9 |
| srr3c | Soybean 8-Day-Old Root | srr3c.pk002.a8 |
| wl1n | Wheat Leaf From 7 Day Old Seedling* | wl1n.pk0027.f4 |
| wre1n | Wheat Root From 7 Day Old Etiolated Seedling* | wre1n.pk0015.d10 |

*These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adarns et al., (1991) *Science* 252:1651–1656). The resulting ESTs are analyzed using a Perkin Elmer Model 377 fluorescent sequencer.

Example 2

Identification of cDNA Clones cDNA clones encoding protein disulfide isomerases were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Protein Disulfide Isomerase Precursor The BLASTX search using the EST sequences from clones listed in Table 3 revealed similarity of the polypeptides encoded by the cDNAs to protein disulfide isomerase precursor from *Humicola insolens* or *Bos taurus* (NCBI General Identifier Nos. 1709618 and 129726, respectively). Shown in Table 3 are the BLAST results for individual ESTs ("EST"), or the sequences of the entire cDNA inserts comprising the indicated cDNA clones ("FIS"):

TABLE 3

BLAST Results for Sequences Encoding Polypeptides Homologous to Protein Disulfide Isomerase Precursor

| Clone | Status | NCBI General Identifier No. | BLAST pLog Score |
|---|---|---|---|
| cr1n.pk0090.d2 | EST | 1709618 | 55.52 |
| srr3c.pk002.a8 | EST | 1709618 | 48.52 |
| csi1.pk0032.c9:fis | FIS | 129726 | 28.04 |

The data in Table 4 represents a calculation of the percent identity of the amino acid sequences set forth in SEQ ID NOs:2, 4 and 6 and the *Humicola insolens* and *Bos taurus* sequences (NCBI General Identifier Nos. 1709618 and 129726, respectively).

TABLE 4

Percent Identity of Amino Acid Sequences Deduced From the Nucleotide Sequences of cDNA Clones Encoding Polypeptides Homologous to Protein Disulfide Isomerase Precursor

| | Percent Identity to | |
|---|---|---|
| SEQ ID NO. | 1709618 | 129726 |
| 2 | 80.0 | 42.7 |
| 4 | 17.0 | 22.2 |
| 6 | 50.0 | 37.3 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of two corn and one soybean protein disulfide isomerase precursor. These sequences represent the first corn and soybean sequences encoding protein disulfide isomerase precursor.

Example 4

Characterization of cDNA Clones Encoding RB60

The BLASTX search using the EST sequences from clones listed in Table 5 revealed similarity of the polypeptides encoded by the cDNAs to RB60 from *Chlamydomonas reinhardtii* and to the putative protein disulfide isomerase-like protein from *Arabidopsis thaliana* resulting from the EU Arabidopsis sequencing project (NCBI General Identifier Nos. 2708314 and 4678297, respectively). Shown in Table 5 are the BLAST results for individual ESTs ("EST"), the sequences of the entire cDNA inserts comprising the indicated cDNA clones ("FIS"), or contigs assembled from an FIS and one or more ESTs ("Contig*"):

TABLE 5

BLAST Results for Sequences Encoding Polypeptides Homologous to RB60

| | | BLAST pLog Score | |
|---|---|---|---|
| Clone | Status | 2708314 | 4678297 |
| fds.pk0022.c11 | FIS | 101.00 | >254.00 |
| Contig of: | Contig* | 95.00 | 157.00 |
| cen3n.pk0155.e7 | | | |
| cs1.pk0100.a7 | | | |
| p0032.crcbb52r | | | |
| p0125.czabp07r | | | |
| cs1.pk0077.f10 | FIS | 47.15 | 83.52 |
| sr1.pk0095.e9 | FIS | 34.30 | 31.70 |
| Contig of: | Contig* | 105.00 | >254.00 |
| scr1c.pk005.i17 | | | |
| sdp2c.pk038.e22 | | | |
| sdp3c.pk021.a3 | | | |
| sfl1.pk0026.h1 | | | |
| sl2.pk0075.b10 | | | |

TABLE 5-continued

BLAST Results for Sequences Encoding Polypeptides Homologous to RB60

| | | BLAST pLog Score | |
|---|---|---|---|
| Clone | Status | 2708314 | 4678297 |
| w11n.pk0027.f4 | EST | 58.30 | 59.09 |
| wre1n.pk0015.d10 | FIS | 59.00 | 92.00 |

The sequences from clones w11n.pk0027.f4 and sr1.pk0095.e9 also showed similarity to the predicted gene encoded by the contig of the rice ESTs D22477 and AU75323. The data in Table 6 represents a calculation of the percent identity of the amino acid sequences set forth in SEQ ID NOs:8, 10, 12, 14, 16, 18 and 20 and the *Chlamydomonas reinhardtii* and *Arabidopsis thaliana* sequences (NCBI General Identifier Nos. 2708314 and 4678297).

TABLE 6

Percent Identity of Amino Acid Sequences Deduced From the Nucleotide Sequences of cDNA Clones Encoding Polypeptides Homologous to RB60

| | Percent Identity to | |
|---|---|---|
| SEQ ID NO. | 2708314 | 4678297 |
| 8 | 35.5 | 58.8 |
| 10 | 32.0 | 47.9 |
| 12 | 39.5 | 66.4 |
| 14 | 28.3 | 25.9 |
| 16 | 34.8 | 57.0 |
| 18 | 27.3 | 25.9 |
| 20 | 35.4 | 53.4 |

Sequence alignments and percent identity calculations were performed using the Megalign gram of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a balsam pear, two corn, two soybean and two wheat RB60. These sequences represent the first balsam pear, corn, soybean and wheat sequences encoding RB60.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML 103. Plasmid pML 103 has been deposited under the terms of the Budapest Treaty at ATCC (American Type Culture Collection, 10801 University Blvd., Manassas, Va. 20110–2209), and bears accession number ATCC 97366. The DNA segment from pML 103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 6

Expression of Chimeric Genes in Dicot Cells

A seed-specific expression cassette composed of the promoter and transcription terminator from the gene encoding the β subunit of the seed storage protein phaseolin from the bean Phaseolus vulgaris (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70–73, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from E. coli; Gritz et al.(1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 $\mu$L of a 60 mg/mL 1 $\mu$m gold particle suspension is added (in order): 5 $\mu$L DNA (1 $\mu$g/$\mu$L), 20 $\mu$l spermidine (0.1 M), and 50 $\mu$L CaCl$_2$ (2.5 M). The particle preparation is then agitated for three minutes, spun in a microfuge for 10 seconds and the supernatant removed. The DNA-coated particles are then washed once in 400 $\mu$L 70% ethanol and resuspended in 40 $\mu$L of anhydrous ethanol. The DNA/particle suspension can be sonicated three times for one second each. Five $\mu$L of the DNA-coated gold particles are then loaded on each macro carrier disk.

Approximately 300–400 mg of a two-week-old suspension culture is placed in an empty 60×1 5 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 $\mu$g/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 $\mu$L of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 $\mu$g/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 $\mu$L of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One $\mu$g of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a polypeptide having disulfide isomerase activity, wherein the amino acid sequence of the polypeptide and the amino acid sequence of SEQ ID NO:10 have at least 90% identity, or
   (b) the complement of the nucleotide sequence, wherein the complement and the nucleotide sequence contain the same number of nucleotides and are 100% complementary.

2. The polynucleotide of claim 1 wherein the amino acid sequence identity is at least 95%.

3. The polynucleotide of claim 1 wherein the polypeptide comprises the amino acid sequence of SEQ ID NO:10.

4. The polynucleotide of claim 1 wherein the polynucleotide comprises the nucleotide sequence of SEQ ID NO:9.

5. A chimeric gene comprising the polynucleotide of claim 1 operably linked to at least one regulatory sequence.

6. A seed comprising the chimeric gene of claim 5.

7. A cell comprising the polynucleotide of claim 1.

8. The cell of claim 7, wherein the cell is selected from the group consisting of a yeast cell, a bacterial cell and a plant cell.

9. A transgenic plant comprising the polynucleotide of claim 1.

10. A virus comprising the polynucleotide of claim 1.

11. A method for transforming a cell comprising introducing into a cell the polynucleotide of claim 1.

12. A method for producing a transgenic plant comprising (a) transforming a plant cell with the polynucleotide of claim 1 and (b) regenerating a plant from the transformed plant cell.

13. A vector comprising the polynucleotide of claim 1.

14. A method for isolating a polypeptide encoded by the polynucleotide of claim 1 comprising isolating the polypeptide from a cell transformed with said polynucleotide.

* * * * *

UNITED STATES PATENT AND TRADEMARK OFFICE
CERTIFICATE OF CORRECTION

PATENT NO. : 6,864,403 B1 Page 1 of 1
APPLICATION NO. : 09/417251
DATED : March 8, 2005
INVENTOR(S) : Rebecca E. Cahoon et al.

It is certified that error appears in the above-identified patent and that said Letters Patent is hereby corrected as shown below:

Title page of patent, item (75) Inventors section: delete "Guo-Hua Miao, Hockessin, DE (US);"

Signed and Sealed this

Twenty-seventh Day of February, 2007

JON W. DUDAS
*Director of the United States Patent and Trademark Office*